United States Patent [19]

Van Dijk

[11] Patent Number: 4,869,887

[45] Date of Patent: Sep. 26, 1989

[54] INTEGRATED AMMONIA-UREA PROCESS

[76] Inventor: Christiaan P. Van Dijk, 10722 Glenway, Houston, Tex. 77070

[21] Appl. No.: 115,242

[22] Filed: Oct. 30, 1987

[51] Int. Cl.$^4$ ..................... C01C 1/04; C07C 126/00
[52] U.S. Cl. ...................................... 423/359; 564/67; 564/69
[58] Field of Search ................... 423/359; 564/67, 69

[56] References Cited

U.S. PATENT DOCUMENTS

| | | |
|---|---|---|
| 27,377 | 5/1872 | Otsuka et al. . |
| 2,087,980 | 7/1937 | Lawrence .............................. 564/67 |
| 3,303,215 | 2/1967 | Otsuka et al. ......................... 564/67 |
| 3,310,376 | 3/1967 | Cook et al. . |
| 3,371,115 | 2/1968 | Cook et al. . |
| 3,372,189 | 3/1968 | Otsuka et al. . |
| 3,607,939 | 9/1971 | Kaasenbrood et al. . |
| 3,647,872 | 3/1972 | Kaasenbrood et al. . |
| 3,674,847 | 7/1972 | Kaasenbrood et al. . |
| 4,012,443 | 3/1977 | Bonetti . |
| 4,138,434 | 2/1979 | Lagana et al. . |
| 4,235,816 | 11/1980 | Lagana et al. . |
| 4,291,006 | 9/2982 | Pagani et al. . |
| 4,320,103 | 3/1982 | Pagani . |
| 4,613,696 | 9/1986 | Zardi ..................................... 564/67 |

FOREIGN PATENT DOCUMENTS

| | | | |
|---|---|---|---|
| 1468732 | 12/1968 | Fed. Rep. of Germany ........ 564/69 |
| 1816099 | 7/1969 | Fed. Rep. of Germany ........ 564/69 |
| 1494555 | 9/1967 | France .................................... 564/69 |

OTHER PUBLICATIONS

"The Urea Stripping Process-The Tecnical Manufacture of Urea, with Carbon Dioxide Used Both as Reactant and as Stripping Gas", by P. J. C. Kassenbrood, 4th European Symposium, Chem. Reaction Engineers, Brussels, 09/06, pp. 1-8.

"Integrating Ammonia and Urea Production", by Douglas Keens, 01/08/82, I. Chem. E. Symposium Series No. 74, pp. 55-65.

Primary Examiner—John Doll
Assistant Examiner—Wayne A. Langel
Attorney, Agent, or Firm—Kurt S. Myers

[57] ABSTRACT

An integrated ammonia urea process where the reaction of carbon dioxide and ammonia is in a urea reactor having a condensing section, a reaction section having more than one stage and a stripping section. The raw ammonia synthesis gas containing carbon dioxide is introduced into the stripping section of the urea reactor at a pressure selected within the range of 2000 and 3500 psig. The stripping effluent removed from the stripping section comprises the raw ammonia synthesis gas, carbon dioxide and ammonia which is introduced into a state of the reaction section.

4 Claims, 2 Drawing Sheets

INTEGRATED AMMONIA-UREA PROCESS

BACKGROUND OF THE INVENTION

1. Field of the Invention

The present invention is directed to an integrated ammonia-urea process. More specifically, the present invention is directed to a process wherein the urea reaction of reacting carbon dioxide and ammonia is carried out in a reactor in the presence of raw ammonia synthesis gas. In the process of the present invention the urea reactor has a condensing section, a reaction section with more than one stage and a stripping section. The raw synthesis gas containing carbon dioxide is introduced into the stripping section of the urea reactor at a pressure within the range of about 2000 to 3500 psig.

2. Prior Art

The combination of an ammonia plant and a urea plant is common since the production of urea involves the reaction of two moles of ammonia for each mole of carbon dioxide. Commercially the combination of plants are relatively independent, i.e., the ammonia plant produces the ammonia and usually the carbon dioxide necessary for reaction in the urea plant. Various attempts have been made to integrate the two plants so that the two operations are integrated rather than merely combined.

U.S. Reissue 27,377 discloses an integration wherein the ammonia synthesis gas containing carbon dioxide is passed into a carbon dioxide absorber and the gases then passed on to the ammonia synthesis reactor. The carbon dioxide extracted in an ammonia and water solution is then reacted in the urea synthesis reactor.

The foregoing patent illustrates the basic integration which has been carried out in the prior art. The distinctions in the integrated processes have been primarily the definition of the specific stream utilized to extract the carbon dioxide from the reactant gases U.S. Pat. No. 3,310,376 and U.S. Pat. No. 3,371,115 are both patents assigned to Chemical Construction Company showing various manners in which the carbon dioxide is extracted from a gas which is then reacted to form ammonia.

U.S. Pat. No. 3,372,189 assigned to Toyo Koatsu Industries likewise discloses extracting the carbon dioxide from an ammonia synthesis gas which is characterized by adjusting the mole ratio of ammonia to carbon dioxide in the resulting absorbate to between 2 to 3.6. Accordingly, the scrubbing column which removes the carbon dioxide is maintained under controlled conditions to properly select the composition of the aqueous absorbent solution and the temperature before feeding the aqueous absorbent solution to the scrubbing column.

U.S. Pat. Nos. 4,012,443; 4,138,434; 4,291,006; and 4,320,103 are all assigned to Snam Progetti. Each of these patents are directed to integrated urea-ammonia processes wherein the ammonia synthesis gas is first contacted with an aqueous solution usually containing ammonia to extract the carbon dioxide from the ammonia synthesis gas. U.S. Pat. No. 4,012,443 is specifically directed to utilizing two carbon dioxide absorbers. U.S. Pat. No. 4,138,434 is characterized as an improvement to the SNAM ammonia stripper integrated urea process wherein a gas stream obtained by reforming hydrocarbons is fed to an adiabatic ammonia stripper placed down stream of a carbamate decomposer. U.S. Pat. No. 4,291,006 is directed specifically to a process and apparatus for the absorption of the carbon dioxide in an apparatus which is divided into one section of a plate type absorber and the other section being a thin film type absorber. U.S. Pat. No. 4,320,103 is specifically directed to an improved method which consists in that portion of that gas stream comprising carbon dioxide, hydrogen and nitrogen being fed to the carbon dioxide absorption unit in a specified manner.

U.S. Pat. No. 4,235,816 also assigned to Snam Progetti is specifically directed to absorbing from the stream obtained by steam reforming of hydrocarbons the carbon dioxide in a very concentrated ammonia solution.

U.S. Pat. Nos. 3,607,939 and 3,647,872 both assigned to Stamicarbon are directed to procedures in handling the ammonia feed to the urea reactor. The ammonia synthesis gas referred to in these patents is the gas being removed from the ammonia reactor. It is understood that the process of producing ammonia involves a recycle of the ammonia synthesis gases since there is not a 100% conversion of the hydrogen and nitrogen to ammonia.

An article "The Urea Stripping Process—The Technical Manufacture of Urea, With Carbon Dioxide Used Both as Reactant and as Stripping Gas" by P. J. C. Kaasenbrood given at the Fourth European Symposium of the Chemical Reaction Engineering in Brussels in September 1968, is incorporated herein by reference in its entirety. This article discloses the technical preparation of urea as well as the stripping with carbon dioxide gas. The paper mentions the possibility of inerts but does not disclose any specific gases other than carbon dioxide as the gas for stripping the urea product.

U.S. Pat. No. 3,674,847 assigned to Stamicarbon discloses a process for urea production in combination with ammonia synthesis wherein a raw synthesis gas is utilized by introducing that gas into one of two strippers. The process is disclosed by reference to a urea plant with a capacity of approximately 1,800 metric tons of urea a day operated at a synthesis gas pressure of 350 atmospheres (approximately 5060 psig).

An article "Integrating Ammonia and Urea Production" by Douglas Keens published in I. Chem. E. Symposium, (series number 74) in 1982 is incorporated herein by reference in its entirety. This article discloses a number of proposals for the integration of ammonia and urea production. The author states: "It is curious that full integration of the two processes has not yet taken place on the industrial scale although the principles have been demonstrated as viable. One reason for this might be the unwillingness of compressor manufacturers to guarantee their machines for mixed gas streams containing carbon dioxide with water and/or ammonia present. Another might be the fact that the carbon content of the ammonia feedstock will not always be just right; a 'lean' natural gas will give insufficient carbon dioxide, a petroleum feedstock will give too much. For flexibility, then, auxiliary carbon dioxide removal is needed, or means for handling surplus ammonia production; the increment in capital cost will work against some of the equipment savings made." This conclusion by the author was made after showing that all schemes discussed in the article had substantial reduction in capital cost and energy consumed.

It is still the state of the art that integration of the two processes has not taken place on the industrial scale. The present invention not only has the advantage of lower capital costs and energy savings, but addresses the practical reasons why the integration has not taken place heretofore.

SUMMARY OF THE INVENTION

The present invention is directed to an integrated ammonia urea process. More particularly, the present invention is directed to an integrated ammonia urea process where the reaction of carbon dioxide and ammonia is in a urea reactor having a condensing section, a reaction section having more than one stage and a stripping section. The raw ammonia synthesis gas containing carbon dioxide is introduced into the stripping section of the urea reactor at a pressure selected within the range of 2000 and 3500 psig. The stripping effluent removed from the stripping section comprises the raw ammonia synthesis gas, carbon dioxide and ammonia which is introduced into a stage of the reaction section. More than one stage and preferably three stages are utilized in the reaction section. Into each stage is introduced a hot liquid ammonia stream. In the process of the present invention the ammonia to carbon dioxide ratios are in the order of excess of 6 to 1 wherein the conventional urea process utilizes ratios of 4 to 1 or less.

The significant and practical distinctions of the present invention are that the ammonia and urea conditions of operation are carried out at essentially the same pressure and that those pressures are very close to the presently preferred conditions from a preferred cost standpoint for the production of ammonia or urea. A second advantage is that the process of the present invention eliminates the carbamate pumps which are the main source of corrosion and problems for shutting down the urea process.

Further advantages of the present invention are identified as follows:

1. The temperature at which stripping is carried out is less than 190° C. and can be as low as 160° to 170° C. At the lower temperatures of stripping there is less corrosion and significant savings in energy and capital.

2. The range of pressure is well suited for both urea and ammonia production as presently preferred in separate operations and there is no large pressure difference between ammonia and urea reactors.

3. The recycle of ammonia in the integrated process is carried out mostly by reflux against cooling water, using the heat of reaction as essentially all the heat required for evaporating of the ammonia.

4. The removal of water in the process improves the carbamate conversion. Water is removed from the reaction section by less water being carried to the reaction section due to the lower temperatures in the stripping section and may be by water being removed in the condensing section.

BRIEF DESCRIPTION OF THE DRAWINGS

For a detailed description of a preferred embodiment of the present invention reference will now be made to the accompanying drawings wherein.

PREFERRED EMBODIMENT OF THE INVENTION AND DESCRIPTION THEREOF

Figure 1:
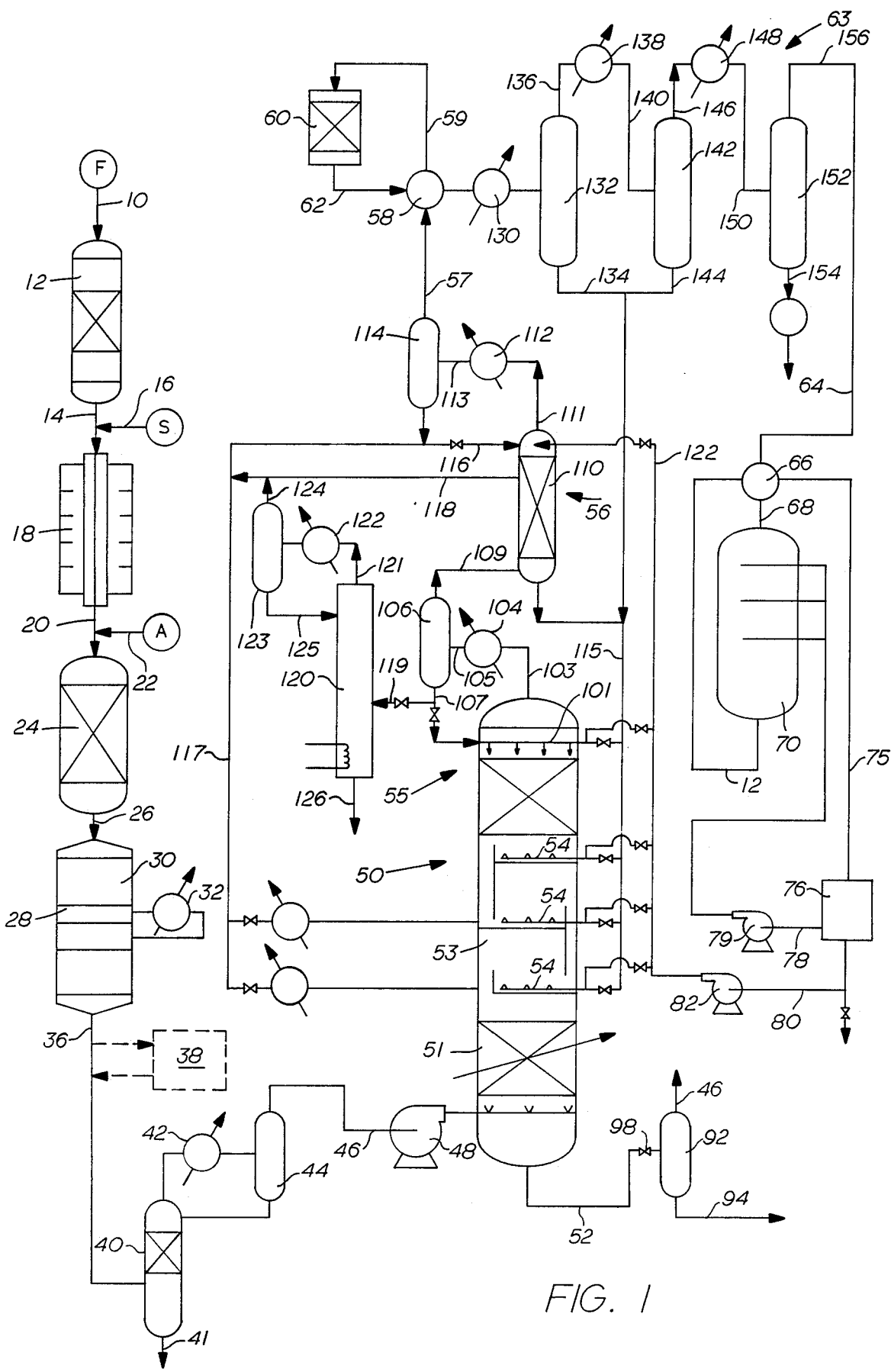
FIG. 1 is a schematic process flow sheet of the integrated ammonia-urea process.

Referring to FIG. 1, wherein a preferred embodiment of the process of the present invention is set forth, the flowsheet depicts the urea reactor placed within the ammonia flowsheet with the raw ammonia synthesis gas passing through the urea reactor.

More specifically, a hydrocarbon feed, preferably natural gas, is introduced by line 10 to a desulfurizer 12. Any sulfur such as hydrogen sulfide is removed from the gas and the desulfurized gas is removed by line 14. Steam is added to the desulfurized hydrocarbon stream 14 by line 16. The combined streams are introduced to a primary reformer 18 containing reforming catalyst. In the primary reformer the hydrocarbon gases such as methane, ethane, etc. and excess steam are heated to temperatures which cause catalytic conversion to form hydrogen, carbon monoxide and some carbon dioxide. The reformed gas stream, which contains some unconverted feed, is removed by line 20. To the gas stream 20 is added air by line 22. The combined streams are then introduced into a secondary reformer 24 also containing reforming catalyst. In the secondary reformer 24, the oxygen in the air burns the unconverted feed, raising the temperature of the hydrocarbon-steam mixture to form more hydrogen, carbon monoxide and carbon dioxide. The almost totally reformed gas is removed from the secondary reformer by line 26. The gas in line 26 is introduced into a two stage shift reactor 28. In the shift reactor most of the carbon monoxide is converted to carbon dioxide as the gases pass through the bed(s) of shift catalyst. The shift reactor 28 may have a first bed 30 of catalyst, after which the gases are cooled in heat exchanger 32 before being introduced to a second bed 34 of shift catalyst. The gases are removed from the shift reactor 28 by line 36.

In the conventional ammonia plant, the gases which at this point consist of hydrogen, nitrogen, carbon dioxide, argon, and small amounts of carbon monoxide and methane are usually introduced into a carbon dioxide removal step (shown in dotted lines) 38. The usual carbon dioxide removal processes are extractions with selected solvents which remove almost all the carbon dioxide from the remaining gases.

Without the carbon dioxide removal step 38, the gases in line 36 may contain traces of water which are removed by passing them through a countercurrent condensor 40. Water and any ammonia which may be present (especially during start up) are condensed and removed by line 41. The gas stream is removed from the condensor 40 and cooled in heat exchanger 42 and introduced into a separator 44. The liquid from separator 44 is introduced into the top of condensor 40. The gas stream is introduced into a compressor 48. The gas stream introduced into compressor 48 is referred to as "raw ammonia synthesis gas" and carbon dioxide. The term "raw ammonia synthesis gas" is used to refer to a gas stream which has not passed through an ammonia reactor and has a composition of gases which include hydrogen, nitrogen and small amounts of carbon monoxide, argon and possibly methane. Further, the mole ratio of hydrogen and nitrogen is such that there are approximately three moles of hydrogen for every mole of nitrogen.

The compressor 48 is a conventional centrifical compressor usually having more than one stage. In that the gases introduced to the compressor as contrasted to the centrifical compressor used conventionally in an ammonia process, contain carbon dioxide there is the possibility of having a slightly corrosive gas stream, especially at low temperatures. Accordingly the inlet and possibly the outlet, and the intercooler, where the gases may be relatively cool is made of a non-corrosive steel such as one of the known stainless steels.

The combination of the countercurrent condensor 40 together with the stainless items in and to the centrifical compressor will overcome the problem attributed to the compressor manufacturer as set forth in the Keens' article.

It is preferred that the hydrocarbon feed material to the process is natural gas which is substantially methane. However, the process can be carried out on heavier hydrocarbon gases as well as liquid hydrocarbons. As the hydrocarbons become heavier than methane more carbon dioxide will be produced in the processes required to produce a raw ammonia synthesis gas. It may be necessary depending upon the hydrocarbon feed used in the integrated process of the present invention to remove some carbon dioxide to maintain the balance of carbon dioxide to the amounts of hydrogen and nitrogen available for ammonia in order to provide the stoichiometry of the urea reaction, i.e. at least two moles of ammonia to each mole of carbon dioxide. In the event some carbon dioxide must be removed the carbon dioxide removal step 38 may be required but only to remove the excess carbon dioxide. This removal step is an operation low in capital and energy. Furthermore, it should be understood that while a conventional scheme uses natural gas for producing ammonia synthesis gas, the gases may also come from coal gasification or some other process which produces a raw ammonia synthesis gas and carbon dioxide.

The essence of the standard preparation of urea consist in reacting ammonia and carbon dioxide at elevated pressure and temperature. Initially a liquid phase is formed in which the reactants are contained largely in the form of ionized ammonium carbamate or simply referred to as carbamate. By dehydration, the carbamate is converted to urea. The condensation reaction of 2 moles of ammonia with 1 mole of carbon dioxide is a fast heterogeneous, highly exothermic reaction. On the other hand, the formation of urea is a slow endothermic equilibrium reaction which proceeds in the liquid phrase wherein the carbamate is in equilibrium with urea and water. It is desired to carry out the dehydration reaction at temperatures above 160° C. since the reaction rates then are acceptable for the formation and later recovery of urea.

The raw ammonia synthesis gas and carbon dioxide are introduced to a urea reactor 50. In the process of the present invention the pressure to which the combined raw ammonia synthesis gas and carbon dioxide are compressed is in a pressure range between 2000 and 3500 psig. It is preferred that the process be carried out at pressures between 2500 and 3000 psig. One importance of the pressure is that this range of pressure is an optimum range both for the production of ammonia and urea. Also at this pressure range it has been unexpectly found that improvements can be made within the urea process. Again the pressure is a significant factor in the integration of the ammonia and urea processes according to the present invention.

The urea reactor 50 is made up of a stripping section 51, a reaction section 53 and a condensing section 55. The raw ammonia synthesis gas and carbon dioxide are introduced into the stripping section 51 of the urea reactor 50. In the process of the present invention, countercurrent flow is utilized between the gas which flows upwardly and the liquid which flows downwardly. Additionally, the flow downwardly in urea reactor 50 is all gravity flow. Thus, urea reactor 50 of the present invention has the stripping section 51 below and the condensing section 55 above the reaction section 53. The reaction section 53 may be a single vessel or a plurality of vessels. The fluids within a particular vessel may flow cocurrent but the overall flow in the urea reactors is in a countercurrent scheme.

The introduction of a raw ammonia synthesis gas and carbon dioxide to a urea reactor would seem disadvantageous. The presence of the raw ammonia synthesis gas, which is a diluent gas in the reactor, is disadvantageous since to attain sufficient conversion of the carbon dioxide a high ammonia partial pressure in the reactor is necessary. This means that a large amount of ammonia has to be evaporated at the pressure in which the process operates. As the overall pressure is reduced, the relative amount of ammonia increases. This apparent disadvantage of having the raw ammonia synthesis gas present has been overcome according to the present invention.

According to the process of the present invention the temperature which is desired in the stripping section 51 is at a temperature within the range of about 160° to about 190° C., preferably between 160° and 170° C. The most significant advantage in maintaining the temperature within this range of 160° to 170° C. is that corrosion is not as severe as when the temperature exceeds about 175° C. Further, when higher temperatures are required, the energy requirements may be substantially increased.

The raw ammonia synthesis gas and carbon dioxide introduced into the stripping section 51 of the urea reactor 50 acts to strip unreacted ammonia and carbon dioxide as well as some water from the liquid urea passing counter-current in the stripping section 51. It has been found according to the present invention that the stripping gas, which is the raw ammonia synthesis gas and carbon dioxide, at the conditions in the stripping section 51 strip the carbon dioxide and ammonia without major amounts of water. Therefore, the effect on carbamate formation in the reaction section 53 is relatively insignificant. Further, the presence of the raw ammonia synthesis gas allows stripping with the carbon dioxide at substantially the same total pressure as in the reactor, but at a considerably lower carbon dioxide partial pressure. This permits the stripping to be carried out at lower stripping temperatures. Finally, the presence of the raw ammonia synthesis gas in the stripping gas lifts the ammonia and the liquids throughout the reactor. The conditions in the stripper are such that good stripping results and essentially no carbon dioxide escapes with the liquid.

The effluent gas stream from the stripping section 51 which contains increased amounts of carbon dioxide, ammonia and water is introduced into a stage of the reaction section 53 of the urea reactor 50. The reaction section 53 may have all stages in one vessel or in more than one vessel. As illustrated in FIG. 1 there is depicted three stages in the reaction section 53 as each liquid tray represents a stage. While three stages are shown two or more stages can be used. It is to be understood that the carbamate and urea formation reactions are occurring throughout the reactor in varying degrees. The formation of the carbamate is predominant in the second of three stages and it should be understood that due to the exothermic nature of that reaction substantial amounts of heat are produced. As will be described in more detail hereinafter ammonia is being introduced to each stage of the reaction section 53. The process also requires substantial recycle of ammonia and the ammonia is recycled hot. In contrast to conventional urea processes where the ratios of ammonia to carbon dioxide are less than four to one the process of the present invention maintains the ratio of ammonia to carbon dioxide in excess of six to one.

It is preferred in the process of the present invention that the stripping gas which comprises the raw ammonia synthesis gas and carbon dioxide is introduced after compression and not cooled. The temperature in the first stage of the reaction section 53 is close to 160° C. where the formation of urea proceeds with acceptable rates. The later stages where the condensation reaction is occurring which is highly exothermic are carried out so as to volatilize especially the ammonia, but also water, both present in the liquid phase, to remove these materials in the gaseous phase.

In the condensing section 55 of the urea reactor the water, carbon dioxide and ammonia are condensed. The condensing section 55 may include a portion within a single vessel containing the reaction section 53 and a condensing configuration outside the vessel as represented by condenser section 56. The specifics of the condensing section 55 will be described in more detail hereinafter. It should be understood according to the present invention that the condensing section 55 has more than the purpose to remove from the ammonia synthesis gas the carbon dioxide, ammonia and substantial amounts of water to form a suitable ammonia synthesis gas. The obvious purpose is to condense the carbon dioxide, the ammonia and the water from the gas stream. In the process of the present invention the gases are moving countercurrent to the reacting liquids. The liquid is formed in the reflux out of water, ammonia and carbon dioxide, all present in the vapor. Under the conditions of the present invention the ammonia partial pressure is such that the ammonia is close to the super critical condition, thus enhancing water "solubility" in the gas. This allows very low carbon dioxide leakage from the condensing section 55 by condensation of the carbon dioxide as carbamate. After removal of the carbon dioxide, the gas stream contains ammonia and water which is condensed. The water can be removed from the process in the condensing section 55 by separating from ammonia by distillation. Thus, the process may be run with total reflux but it is also possible that between 30% and 90% of the water of reaction is removed from the system in the condensing section 55. When the water is removed in the condensing section, it has a direct effect of a substantial increase in carbamate conversion. Further, as a significant advantage, it lowers the heat duty in the stripping section 51. With the removal of the carbon dioxide, ammonia and substantial amounts of water, a gas stream of ammonia synthesis gas is produced which is removed from this section by line 57.

This gas is passed through a heat exchanger 58 and then introduced by line 59 to a methanator 60. The methanator 60 converts the small trace amounts of carbon monoxide and carbon dioxide with hydrogen present in the stream to methane. This is necessary since carbon monoxide and carbon dioxide are poisons to the ammonia catalyst whereas methane acts as an inert. The synthesis gas is removed from methanator 60 by line 62 and passed in exchange with the entry gas through heat exchanger 58. The gas then enters a condensing zone 63 which comprises a series of heat exchangers for cooling the gas and removing condensates which is mostly ammonia, but also includes water to obtain a dry ammonia synthesis gas in line 64. Again the details of the condensing zone 63 will be set forth in more detail hereinafter. The ammonia synthesis gas in line 64 is passed through a heat exchanger 66 and removed by line 68 for introduction into an ammonia reactor 70. In the ammonia reactor the hydrogen and nitrogen react to form ammonia. The effluent from the ammonia reactor is removed by line 72 and is passed in indirect heat exchange with the entry gas by passing it through heat exchanger 66 where the cooled gas is removed by line 74 into an ammonia recovery section 76. The ammonia recovery section cools the gas to obtain ammonia as a liquid which requires that the gas be cooled in stages to temperatures of about −10° C. As the total gas is cooled the ammonia is also separated from the synthesis gas, that is the hydrogen, nitrogen, and argon mixture, which is separated and removed by line 78, having a bleed line, and is placed in a compressor 79 to be recycled in split streams into the ammonia reactor 70. Most of the cooled ammonia is removed by line 80 where it is introduced to a compressor 82 for reintroduction into the urea reactor 50. A small excess of ammonia may be bled out of line which may be used as such, in known manners.

In the description of the present invention, an overview of the integrated process has been described. The details of the process steps conventionally associated with the ammonia process are all well within the skill of the art. The details of the specific reforming apparatus or ammonia reactor shown are only illustrative. Accordingly the details of conditions and temperatures are known and it should be understood that the specific configurations of devices shown are not to be considered a limitation on the process of the present invention. It should be understood that if a new ammonia-urea integrated plant according to the present invention were to be designed each of these process steps may be optimally designed to achieve a desired capacity of urea. In addition, considerable savings in both capital and energy are accomplished over the existing proposed combinations of ammonia and urea. On the other hand the present invention can be incorporated into an existing ammonia plant provided that the ammonia synthesis conditions are within the pressure ranges of the present invention. In this event there are still advantages in the process of the present invention.

The stripping section 51 of the urea reactor 50 may be constructed as a heat exchanger wherein the stripping is carried out in tubes with the liquid running down the wall of the tubes, which are in a vertical position. The gas is introduced across a header to flow upward through the tubes whereas the liquid flows by gravity down the inside wall of the tubes. The temperature is maintained by introducing steam to the outside of the tubes and removing a condensate (not shown). The liquid from the stripping section 51 is removed by line 52. The treatment of the liquid urea stream 52 may be carried out conventionally to obtain the urea as a solid either in pril or in flakes. The stream is normally passed through a pressure reduction valve 98 into a separation vessel 92 wherein the liquid stream is removed by line 94 and the gaseous stream which contains water and ammonia is removed by line 96. The details of further removing the water from the liquid stream 94 to obtain the solid urea are conventional. Likewise the gaseous stream of water and ammonia may be recompressed for reintroduction into the urea reactor 50. It is noted that the only compression required in the process of the present invention is an ammonia or ammonia-water stream, thus eliminating carbamate pumps.

The design of the stripping section 51 as a piece of apparatus can be like that disclosed in the article of P. J. C. Kaasenbrood referred to herein above. That article however while stripping with carbon dioxide makes no reference to the inclusion of the stripping gas also including a raw ammonia synthesis gas.

The reaction section 53 of the urea reactor 50 may be a gas liquid contactor as shown in FIG. 1. Each tray represents a stage with the gases passing through the liquids for intimate contact. On each tray is an ammonia injector 54. In the reaction section 53 the carbon dioxide and ammonia are reacting in liquid phase to form carbamate. The carbamate is then dehydrating to form urea and water. As compared to conventional urea processes the amount of ammonia is in large excess. Most of this ammonia is in the gaseous phase. Most or all of the exothermic heat produced in the condensation reaction is utilized to bring excess ammonia from the liquid phase into the gaseous phase. Some extra heat may be necessary for the preheating of the ammonia.

The gaseous phases pass upward in the urea reactor 50 of FIG. 1 into the condensing section 55. The first condensation may occur in the same reactor vessel or can be accomplished completely outside the vessel in which the reactions occur. As illustrated in FIG. 1 a packed bed with counter-current flow has a recirculation of cooled liquid introduced by line 101 to contact the gases in this first countercurrent condensor. The gases from the first condensor are removed out from the vessel by line 103. The gases are then cooled in heat exchanger 104 and introduced by line 105 into a separation vessel 106. The condensed liquids are returned via line 107 to the line 101. The gases are removed from separation vessel 106 by line 109 and introduced into a second countercurrent condensor 110. In countercurrent condensor 110 ammonia and water are condensed. The gases are removed over head by line 111 and cooled in heat exchanger 112. The gases are then introduced by line 113 into a separation vessel 114. The liquids from the condensor 110 are removed by line 115 for reintroduction into the urea reactor 50. The control of the precise recycle of the hot ammonia to the urea reactor 50 is by valves (not numbered).

Returning to the separation vessel 114, the gases are removed by line 57 for introduction to the methanator 60 as explained hereinabove. The liquid from separation vessel 114 is returned as reflux by line 116 to the top of the condensor 110. Also liquid can be returned to the urea reactor by line 117. Control as to which stage is by valves (not numbered) and the individual lines may have heat exchange for heating the returned liquid, if necessary.

An option may be to remove a middle stream from the condensor 110 by line 118 for return to the urea reaction section 53. The side stream would be much dryer than taking a bottom stream for recycle to the reaction section 53.

Attention is now directed to the liquid stream of 107 wherein alternately by line 119, a part of this liquid stream is introduced into a distillation column 120. The liquid in this stream, ammonia, and water may be heated in the distillation column 120 to separate the ammonia overhead in line 121. The gaseous ammonia is cooled in 122 and introduced into a separation vessel 123. Ammonia may be removed by line 124 which may be recompressed for reintroduction into the urea reactor 50. The liquid is removed from the separation vessel 123 by line 125 for reintroduction into the top of the distillation column 120. Water is removed at the bottom of column 120 by line 126. The inclusion of the distillation column 120 permits water to be removed from the urea reactor. Thus, the process can be operated in total reflux meaning not utilizing the distillation column 120 or as much as 30 to 90% of the water formed in the reaction can be removed overhead in what is termed a partial reflux. While not shown, it is understood that other ammonia water mixtures can be added to the distillation column other than from line 107. In the condensing section 55 it is the purpose to remove all of the carbon dioxide in the presence of large excessive amounts of the ammonia and some water, resulting in a carbamate solution for recycle to the urea reactor 50 by gravity. The gases in the gas stream 57 now include only the ammonia synthesis gas, ammonia and small amounts of water, together with only traces of carbon monoxide and possibly also carbon dioxide.

As mentioned herein before, with carbon monoxide and possibly carbon dioxide present in the gases, the gases are passed through a methanator 60 to convert the carbon monoxide and possibly also carbon dioxide to methane. The gases are then passed through heat exchanger 58 for introduction into another heat exchanger 130 which is part of the condensing zone 63. There the gases are cooled condensing liquid ammonia and water removed from separator 132 by line 134. The gases are removed from separator 132 by line 136 and passed through another heat exchanger 138 where the gases are removed by line 140 for introduction into a second separator 142. Again, ammonia and water, if present, is removed by line 144. The liquids from lines 134 and 144 may be combined and introduced to the top of condensor 110. The gases are removed from the separation 142 by line 146 and passed through a third heat exchanger 148. The gases are removed from the heat exchanger 148 by line 150 for introduction into separator 152. At this point using refrigeration only, ammonia is removed and recovered by line 154. The gases from separator 152 are completely dry, all water and ammonia being removed, and are passed by line 156 to line 64 for introduction into the ammonia reactor 70.

Figure 2:
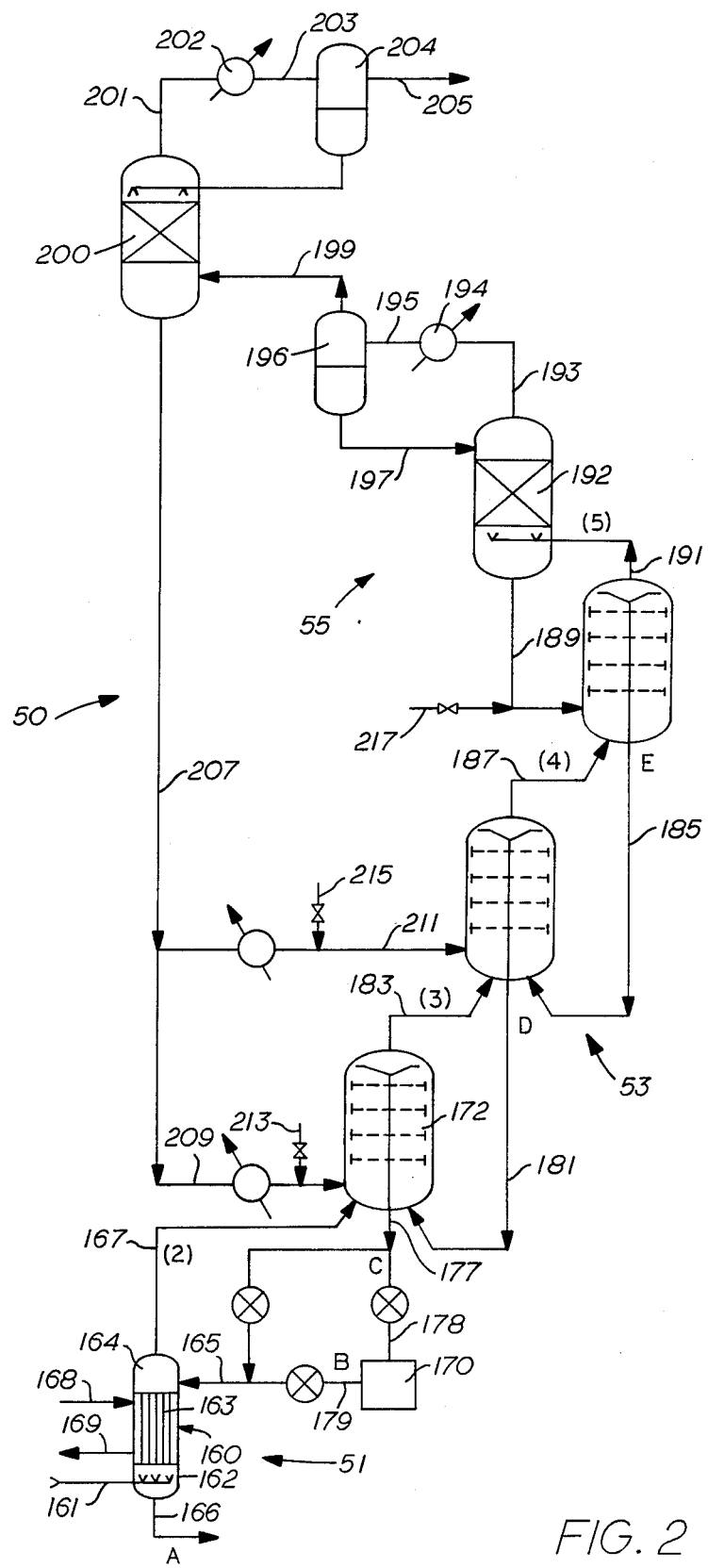
FIG. 2 is a schematic flow sheet showing an embodiment where the urea reaction section has a plurality of vessels.

Referring now to FIG. 2, the urea reactor 50 may be made up of several independent vessels. In the embodiment of FIG. 2 the stripping section 51 is a separate vessel, the reaction section 53 has four independent vessels and three stages, and the condensing section 55 is made up of several independent vessels. In the embodiment of FIG. 2 there are identified certain gas (by numbers) and liquid (by letters) streams which will be referred to in one of the following examples.

The stripping section 51 is represented by a vessel 160. Into the vessel 160 is introduced the stripping gas which comprises the raw ammonia synthesis gas and carbon dioxide by line 161. The stripping gas is introduced into a header 162 to pass up through the plurality of vertically positioned tubes 163 to a top header 164. Header 162 is designed to distribute the gas equally among the tubes 163. Liquid from the reaction section 53 is introduced by line 165 into header 164 which is designed to distribute the liquid equally into each of the tubes 163. This liquid which contains the urea and carbamate and excess ammonia passes downward through the tubes 163. Out of the bottom of stripper vessel 160 is removed the liquid product by line 166. Overhead the gas is removed from stripper vessel 160 by line 167, for introduction into the first stage of the reaction section 53. Heat is introduced to stripper vessel 160 by injection of steam by line 168 on the shell side of tubes 163, and condensate is removed by line 169.

The reaction section 53 is represented by four vessels in which there are three stages for reaction. The vessels in reaction section 53 are an after-reaction vessel 170, a first-stage reactor 172, a second-stage reactor 174, and a third-stage reactor 176. The reactors 172, 174 and 176 also illustrate that co-current flow may be carried out within a stage even though the overall flow within the reactor 50 is counter-current. The liquid from the first-stage reactor 172 is removed by line 177. The liquid may be passed through line 178 into the after-reactor 170 and then by line 179 for introduction into the stripper vessel 160 by line 165. Alternatively, it can be passed directly by line 177 into line 165 directly into the stripper vessel 160. Into the first-stage reactor 172 is introduced the liquid from the second-stage reactor 174 by line 181. Additionally, is introduced the effluent gas from the stripper 160 by line 167. Exit liquid and gas flow co-currently up within the reactor 172 with the liquid then flowing down the down-tube for removal by line 177. The gas passes out the top by line 183. Into the second-stage reactor 174 is passed the liquid from the third-stage reactor 176 by line 185, thus again the liquid introduced by line 185 and the gas by line 183 is passed co-currently up through the second-stage reactor 174. The liquid passes into the down-tube and is removed by line 181. The gas from the second-stage reactor 174 is removed by line 187 to be introduced at the bottom of the third-stage reactor 176. There the gas from 174 and the reflux liquid from line 189 is introduced at the bottom of the third-stage reactor 176. Liquid passes down the down-tube and is removed by line 185. The gas is removed from the top of third-stage reactor 176 by line 191 and introduced into a counter-current condenser 192. The counter-current condenser produces a liquid which is removed by line 189 as mentioned hereinabove for introduction into the third-stage reactor 176. The gases from the counter-current condenser 192 are removed by line 193 and passed through a heat exchanger 194. The cooled gases are introduced by line 195 to a separation vessel 196. The liquids are separated and returned by line 197 to the top of the counter-current condenser 192. The gases are removed from separation vessel 196 by line 199 and introduced into a second counter-current condenser 200. The gases from the second counter-current condenser 200 are removed by line 201 to be introduced into a heat exchanger 202. Then the cooled gases are introduced by line 203 to a separation vessel 204. The gases from the separation vessel 204 are removed by line 205 for passage to the methanator. Line 205 is the same as line 57 in FIG. 1. The liquid from the second counter-current condenser 200 is removed by line 207 which may be introduced into either the first-stage reactor 172 by line 209 or into the second-stage reactor 174 by line 211. The control as to which stage and/or how much liquid is introduced to this stage is done by valving (not shown).

In the process of the present invention, substantial recycle of ammonia is required. One feature of the present invention is that ammonia is introduced into each stage of the reactor section 53 at the desired temperature for achieving adibatic reaction within that stage. As illustrated in FIG. 2, most, if not all, of the ammonia pre-heat can be obtained by introducing most of the ammonia from the bottom of the counter-current condenser 200 into the first- and second-stage reactors 172 and 174. In addition, ammonia is introduced by line 213 into line 202 for the first-stage reactor 172 or line 215 into line 211 for the second-stage reactor 174 or by line 217 into line 189 for the third-stage reactor 176. The ammonia added at these lines 213, 215 and 217 may be ammonia-water produced in the condensing section 63 or from the recycle of the ammonia from the ammonia reactor. Referring to FIG. 1, the ammonia from line 80 is cooled and is recompressed in compressor 82 and passed to a header 220. This cooled ammonia as well as ammonia-water produced in the condensing section 63, without being specific in detail, are the sources of ammonia for introduction into the various stages by lines 213, 215 and 217. The cooled ammonia is utilized in temperature control within the stages. More of the cooled ammonia is likely to be introduced into the second-stage or higher due to the exothermic reaction of the carbon dioxide and ammonia to form carbonate taking place in those stages. On the other hand, the flexibility of the process of the present invention provides the availability of both hot and cool ammonia streams for temperature control. Heat exchangers are shown in lines 209 and 211 of FIG. 2, in the event extra pre-heating is necessary to control the reaction temperatures.

The present invention will be further illustrated by the following examples:

EXAMPLE I

The starting stream for the urea production is the gas stream, as produced in a 1000 TPD (ton per day) ammonia plant using methane feed, at the point in the ammonia plant after the reforming and the watergas shift, followed by cooling and water removal. The composition of the gas stream is approximately:

| | |
|---|---|
| 2631.1 MPH $N_2$ | (moles per hour Nitrogen) |
| 7893.4 MPH $H_2$ | (moles per hour Hydrogen) |
| 78 MPH $CH_4$ | (moles per hour Methane) |
| 34 MPH A | (moles per hour Argon) |
| 10636.5 MPH "Inerts" | (as far as urea formation is concerned) |
| 2283.5 MPH $CO_2$ | (moles per hour Carbon Dioxide) |
| Traces of CO | (Carbon Monoxide) |

This gas is compressed in a centrifugal compressor to a pressure of 2705 psig (184 atg) and introduced into the bottom of the urea reactor in the stripping section. The stripping is carried out between 160° and 170° C., the higher temperature being towards the top of the stripping section. The heat for stripping is provided by indirect heating with steam. The liquid to be stripped exits from the after-reactor and is introduced at the top of the stripper. Its temperature at inlet is 160° C. Its composition is:

| | | |
|---|---|---|
| 2283 MPH UR | (urea) |
| 570 MPH AC | (ammonium carbamate or carbamate) |
| 1000 MPH W | (water) |
| 4275 MPH Am | (ammonia) |

-continued

8128 MPH Total

This composition represents the unusually high conversion of slightly more than 80% of carbamate, and this at only a modest excess of ammonia in the liquid. Back calculated to feed, as normally reported in urea literature, the Am to $CO_2$ ratio in this liquid is 3.5, which is close to urea practice. The stripping duty is approximately: $570 \times 28 \times 1800$ (AC)$+4275 \times 10404$ (Am at 750 psia or 51 ata)$+655.8 \times 18000$, or about 85 MM BTU/Hr. The exit liquid contains 2283 MPH UR and 344.2 MPH W. The liquid thus produced is much lower in water content than a standard urea reactor product and can therefore be worked up at much lower energy cost. It is also possible to use the product as such as a concentrated urea solution. Water removed is 85% of the water produced in the reaction. The gas stream at the top of the stripper has as composition:

| | |
|---|---|
| 10636.5 | MPH In (Inerts) |
| 2853.5 | MPH $CO_2$ |
| 5415 | MPH Am |
| 18905 | MPH Dry |
| 655.8 | MPH W |
| 19560.8 | MPH |

This gas stream enters the first stage. This stage is operated with backmixed liquid at a temperature of 170° C. The liquid exits at a temperature of 170° C., is mixed with 2000 MPH ammonia and reacted in the after reactor to the final product as mentioned at a temperature of 160° C. The liquid composition on exiting the first stage is 2000 Ur, 853 AC, 717 W and 2275 Am. It should be mentioned that the residence time for this liquid in the after-reactor is 20 minutes. To the first stage are also fed the effluent from the stage above and a liquid ammonia stream. It is important to point out, that the ammonia stream is heated to such a temperature, that after evaporation of part of the ammonia, reaction of $CO_2$ and ammonia to ammonium carbamate and urea, the final temperature will be 170° C., as desired. The stage therefore is operated adiabatically.

The effluent from the second stage has the following composition: 1000 MPH Ur, 483.5 MPH AC, 717 MPH W, and 2295.4 MPH Am, for a total of 4495.9 MPH. It's temperature is 165° C. The gas out of the first stage has the composition: 10636.5 MPH In, 1484 MPH $CO_2$, 12,952.3 Am, 1655.8 MPH W, total 26,728.6 MPH. The gas has lost 1369.5 MPH $CO_2$, of which 1000 MPH have reacted to urea, while the rest has increased the ammonium carbamate level in the liquid from above. The condensing $CO_2$ has consumed $2 \times 1369.5 = 2739$ MPH Am. Further, the gas has an increase of $12952.3 - 5415 = 7537.3$ Am. A total of 10276.3 MPH Am therefore has to be added. For heat balance purposes all the ammonia added is expected to vaporize first, and then react with $CO_2$.

For the heat balance the first items are the AC condensation, 1369.5 MPH at $28 \times 1800$ BUT/M; the Ur reaction of 1000 MPH at 12,600 BTU each, and the warm-up of the liquid from above, 148,674 #/Hr, at an assumed 0.5 spec ht, and a 9° C. rise. This adds up to a total of 55.754 MM BTU/Hr. Per mole of ammonia this translates to an absorbed heat of 5425 BTU/M. This is obtained by preheating the ammonia to about 127° C., mostly by reflux, or, if necessary, by heat exchange with steam from the ammonia section, for instance.

The residence time in stage one, reactor I, is taken at about 20 minutes.

The next stage, reactor II, is at a temperature of about 165° C. The incoming liquid is at 160° C. and has as composition 427.6 MPH Ur, 219.8 MPH AC, 641.4 MPH W and 1996.4 MPH Am. The gas out of this stage consists of 10636.5 In, 647.9 MPH $CO_2$, 2152.6 MPH W, and 17446.1 MPH Am. In this stage are also fed approximately 19118.3 MPH Am for evaporation and reaction, while a small amount is provided by the difference in ammonia content of liquid in and out.

It should be pointed out, that while the water partial pressure is high, ammonia partial pressure is close to critical. The W/Am ratio in liquid and gas have a ratio of 3.3, which is reasonable this close to critical.

The final stage, reactor III, is reaction to 427.6 Ur, next to 219.8 Ac, 641.4 W and 1996 Am. Gas out is 10636.5 In, 2152.6 W, 266.9 $CO_2$ and 19440, 4 Am. Reflux of Am and W (213.8 MPH) bring back all the $CO_2$. Temperature control in reactors II and III is similar as in reactor I. The residual water (1938.6 MPH) with ammonia is fed to a distillation tower for removal.

This example illustrates partial removal of the water from the condensing section, rather than all water of reaction being removed with the urea.

EXAMPLE II

This example makes reference to FIG. 2. A gas stream having a composition as follows is introduced to the stripping section:

| (1) | | |
|---|---|---|
| | $N_2$ | 187.0 |
| | $H_2$ | 560.9 |
| | $CH_4$ | 2.7 |
| | A | 1.5 |
| | Total | 752.1 |
| | $CO_2$ | |

The following compositions of gases were introduced to the reaction stages, and the composition in terms of gas and liquid resulted making reference to the numbers and letters in FIG. 2. The gas and liquid compositions are set forth (all in moles per hour) in the following table.

| | Gas Compositions | | | |
|---|---|---|---|---|
| | (2) | (3) | (4) | (5) |
| Inerts | 752.1 | 752.1 | 752.1 | 752.1 |
| $CO_2$ | 152.3 | 83.6 | 45.3 | 14.3 |
| $NH_3$ | 294.0 | 815.8 | 964.5 | 1058.0 |
| Water | 27.1 | 98.9 | 128.6 | 139.2 |
| | 1225.5 | 1750.4 | 1890.5 | 1963.6 |

| | Liquid Compositions | | | | |
|---|---|---|---|---|---|
| | A | B | C | D | E |
| Urea | 95.2 | 95.2 | 85.3 | 46.7 | 24.5 |
| Carbamate | - | 57.0 | 67.0 | 36.9 | 20.8 |
| Water | 95.2 | 122.2 | 112.4 | 145.6 | 153.1 |
| $NH_3$ | | 180.0 | 180.0 | 181.2 | 198.1 |
| | 190.4 | 454.4 | 444.7 | 410.4 | 396.8 |

This example illustrates a total water reflux. All the water of reaction exits with the urea formed.

Although the invention is described with respect to certain specific embodiments, the details thereof are not to be construed as limitations except to the extent indicated in the following claims.

I claim:

1. An integrated ammonia-urea process which comprises:

introducing a raw ammonia synthesis gas containing carbon dioxide countercurrently into a stripping section of a urea reactor and removing from said section an effluent stream which comprises raw ammonia synthesis gas, carbon dioxide and ammonia;

introducing said effluent stream into the first stage of a countercurrent reactor section of said urea reactor which comprises at least two stages;

introducing ammonia to each stage of said urea reactor to react with said carbon dioxide at a pressure within the range of 2000 and 3500 psig and remove said carbon dioxide from said raw ammonia synthesis gas; and removing from the last stage of said reactor section of said urea reactor an effluent stream which comprises said raw ammonia synthesis gas, water and carbon dioxide.

2. A process according to claim 1 wherein said urea reactor comprises three stages.

3. A process according to claim 1 which further includes:

removing water and carbon dioxide from the effluent stream from the last stage of said urea reactor.

4. A process according to claim 3 which further includes:

introducing said raw ammonia synthesis gas through an ammonia converter to produce ammonia.

* * * * *